United States Patent [19]

Schramm

[11] 4,401,450

[45] Aug. 30, 1983

[54] ECONOMIC RECOVERY OF ETHYLENE AND/OR PROPYLENE FROM LOW CONCENTRATION FEEDS

[75] Inventor: Walter Schramm, Munich, Fed. Rep. of Germany

[73] Assignee: Linde Aktiengesellschaft, Wiesbaden, Fed. Rep. of Germany

[21] Appl. No.: 301,261

[22] Filed: Sep. 11, 1981

[30] Foreign Application Priority Data

Sep. 11, 1980 [DE] Fed. Rep. of Germany ....... 3034202
Oct. 29, 1980 [DE] Fed. Rep. of Germany ....... 3040777

[51] Int. Cl.³ .............................................. F25J 3/02
[52] U.S. Cl. ........................................ 62/13; 62/17; 62/28; 62/39
[58] Field of Search .................. 62/17, 24, 27, 28, 38, 62/39, 13, 12

[56] References Cited

U.S. PATENT DOCUMENTS

| | | |
|---|---|---|
| 2,855,433 | 10/1958 | Cobb, Jr. .................................. 62/17 |
| 2,886,611 | 5/1959 | King et al. ................................ 62/17 |
| 3,074,245 | 1/1963 | Becker ..................................... 62/12 |
| 3,143,406 | 8/1964 | Becker ..................................... 62/13 |
| 3,169,052 | 2/1965 | Davison ................................... 62/17 |
| 3,192,732 | 7/1965 | Cahn ....................................... 62/17 |
| 3,276,212 | 10/1966 | Ichihara ................................... 62/28 |

Primary Examiner—Frank Sever
Attorney, Agent, or Firm—Millen & White

[57] ABSTRACT

$C_2$-$C_3$ olefins are recovered from a low concentration gaseous feedstream, e.g. a Fischer-Tropsch waste gas. In a first process stage, the weight percent concentration of the olefins is enriched to at least about 25%. One specific enrichment technique includes scrubbing, preferably 2-stage scrubbing, with hydrocarbon scrubbing agents. Another technique comprises condensation of the olefin in regenerators and absorbing same in a purge phase. The resultant enriched stream, in any case, is then subjected to conventional low temperature separation to recover relatively pure individual streams of ethylene and propylene.

20 Claims, 2 Drawing Figures

ECONOMIC RECOVERY OF ETHYLENE AND/OR PROPYLENE FROM LOW CONCENTRATION FEEDS

BACKGROUND OF THE INVENTION

This invention relates to a process and apparatus for the recovery of low-molecular weight olefins from a gaseous stream containing low concentrations of these hydrocarbons and of the corresponding paraffins.

Low-molecular weight olefins, especially ethylene, constitute important starting materials for the chemical industry and are required in large quantities. A conventional large-scale industrial process for the production of ethylene and propylene comprises the pyrolysis of hydrocarbons, using high cracking temperatures and short residence times. Such processes usually lead to a product gas containing, in a typical cracking operation based on naphtha and gas oil, between 20% and 30% by weight of ethylene. This cracked gas, after cooling and separation of condensed less volatile materials, is fractionated into its individual components in a low temperature gas separation facility.

Economically feasible operation of such a low-temperature separation facility requires that the concentration of the desired low-molecular weight olefins in the feed gas be at a concentration of generally at least on the order of about 20% by weight, varying according to plant investment and operating costs of the particular facility as well as to the market price for the final products.

A lower concentration of the olefins generally results in an economically unattractive low-temperature separation, the lower the concentration, the poorer the economics.

In a number of large-scale industrial processes not having a major objective of obtaining low-molecular weight olefins, there are nevertheless by-product or waste gaseous streams produced containing such a low concentration of olefins that the low temperature recovery thereof is not economically feasible. Such a gas is, for example, the waste gas from a Fischer-Tropsch synthesis oriented primarily to the production of hydrocarbons boiling in the gasoline range from a synthesis gas of hydrogen and carbon oxides. The waste gas produced in such a process contains mostly unreacted synthesis gas along with a minor quantity of light hydrocarbons formed during the synthesis, such as methane, ethane, ethylene, propane, propylene, and $C_4$-hydrocarbons. The ethylene or propylene content ranges, for example, at about 2-3 mol-% in a conventional Fischer-Tropsch plant.

Additional information concerning the prior art processes is found in U.S. Pat. No. 2,915,881, discussed in greater detail below.

SUMMARY OF THE INVENTION

An object of the present invention is to provide an economically feasible process for recovering low molecular weight olefins from low concentration feedstreams.

Another object is to provide apparatus for such a process.

Upon further study of the specification and appended claims, further objects and advantages of this invention will become apparent to those skilled in the art.

These objects are attained by providing a process wherein in a first process stage, at least one fraction is obtained from the gaseous feedstream with an increased concentration of the low-molecular weight olefins and of the corresponding paraffins if present; and that the low-molecular weight olefins are thereafter recovered from the thus-produced fraction(s) in a second process stage by low-temperature separation.

According to the invention, a procedure is thus proposed wherein initially an enrichment of all hydrocarbons is effected which lie in the boiling range of the olefins to be recovered. The resultant gaseous streams enriched in the olefins to be obtained can then be further processed by low-temperature separation. By "low molecular weight olefins" is meant $C_2$- to $C_4$-olefins, specifically ethylene and propylene.

Gaseous feedstreams suitable for the process of this invention are preferably those containing at least 2 mol-% ethylene and/or 2 mol-% propylene. Although an enrichment of these olefins is also possible in case of lower concentrations in the gaseous stream, the expenditure for the enriching step at lower concentrations in most cases under prevailing economic conditions becomes so high that an olefin-producing step is economically unjustifiable. Conversely, this invention is most advantageous at the present time when the feedstreams contain not more than about 12, preferably not more than about 8 mol-% ethylene and/or not more than 15, preferably not more than about 10 mol-% propylene.

To ensure an advantageous operation of the subsequently connected low-temperature separation system, it is suitable to proceed with the enrichment in the first process stage to such an extent that at least about 25 mol-% olefins, preferably more than 35 mol-% olefins are present in the concentrate. The proportion of the individual olefins can very in this connection, depending on the composition of the gaseous stream. Thus, when obtaining olefins from the waste gases of a Fischer-Tropsch synthesis, it is advantageous to aim, in the first process stage, for ethylene concentrations of between about 10 and 17 mol-%, in order to obtain a suitable feed for the second process stage. An even further increase in the olefin proportion in the first process stage is desired, as long as no intolerably high expense is required for this purpose in the first process stage, and since higher olefin concentrations even tend to facilitate the separating task in the second process stage.

When processing the waste gas from a Fischer-Tropsch synthesis according to the process of this invention, it is advantageous first to separate carbon dioxide from this gas. This component, present in the waste gas in a high concentration, e.g. 47 mol-%, can be separated conventionally in a preceding process stage. Scrubbing methods or adsorption processes are suitable for this purpose, for example.

Since an individual Fischer-Tropsch synthesis conventionally is based on a feedstock of a synthesis gas produced by the gasification of coal or other heavy, carbon-containing starting materials, the process of this invention constitutes a breakthrough insofar as it provides for the economically feasible production of ethylene and/or propylene as by-products from such feedstocks.

The enriching of the olefins in the first process stage can be conducted by a scrubbing step in one embodiment of the process of this invention. In such a case, it is expedient to utilize scrubbing media which selectively absorbs gaseous low mol rate hydrocarbons. It has proven to be especially advantageous to use hydrocarbons as the scrubbing media, for example hydrocarbons of 4–8 carbon atoms in the molecule.

In an especially favorable embodiment of this invention, the enrichment of the olefins is conducted in a two-stage scrubbing process wherein, in the second scrubbing stage, a lower temperature is ambient than in the first scrubbing stage, the temperature difference being preferably about 15° to 35° C., especially 20° to 30° C., and wherein differing scrubbing media are employed in the two scrubbing stages. The loaded scrubbing media of the individual scrubbing stages are regenerated in separate cycles during which step the components scrubbed out of the gaseous stream are released and can be introduced into the second process stage.

Although a two-stage process for obtaining ethylene from gases rich in $C_2$ has been known from U.S. Pat. No. 2,915,881, this procedure would have considerable disadvantages if applied to the feedstream of the invention having a low olefin content. In the patented method, the raw gas is fed to two series-connected absorption columns utilizing propylene as the scrubbing agent, wherein the temperature in the first scrubbing stage is higher than in the second scrubbing stage. The pressures in the two columns are about 35 bar. Since a $C_2$-rich gas is involved, the compression of the entire gas to this pressure has no deleterious effect. The minor proportion of these hydrocarbons in the gaseous streams to be processed according to this invention would presuppose, if the conventional process were utilized, that here, too, the entire gas be compressed to 35 bar and cooled to relatively low temperatures, namely about $-63°$ C. in the first scrubbing stage and $-73°$ C. in the second scrubbing stage. These operations could only be accomplished with a very great energy expenditure, and would nowise produce an analogous yield of the desired hydrocarbons. Besides, the high proportion of inert components at $-73°$ C. and 35 bar would lead at the head of the second absorber to a loss of about 50% of the $C_3$-hydrocarbons contained in the gas; however, these $C_3$-hydrocarbons are also desirable as a product in such a process.

A particularly advantageous feature of this invention resides in the use of $C_4$-or higher hydrocarbons as the scrubbing medium in the first scrubbing stage and the use of $C_6$- or higher hydrocarbons in the second scrubbing stage. The operation of the first scrubbing step with a scrubbing medium having a lower boiling point has the advantage of requiring a smaller amount of scrubbing medium to scrub out the $C_{3+}$-hydrocarbons. This leads to lower initial investment costs and a lower refigeration loss due to incomplete heat exchange in the heat exchanger between the first scrubbing stage and the associated regenerating column. The desired low-molecular weight olefins can be enriched in concentrations of up to 15–30 mol-%, without having to compress concomitantly an excessive amount of inert compounds. Thus, the hydrocarbons, after enrichment, are present in a concentration permitting economically attractive processing in a downstream low-temperature separation plant.

A preferred scrubbing medium in the first scrubbing stage is butane and in the second scrubbing stage, hexane. This has the advantage that neither the temperatures nor the pressures need to assume extreme values. In this case, $C_{3+}$-hydrocarbons are scrubbed out advantageously in the first scrubbing stage at about $-5°$ to $-25°$ C., preferably about $-20°$ C., and in the second scrubbing stage, $C_2$-hydrocarbons are scrubbed out at about $-30°$ to $-50°$ C., preferably about $-40°$ C. and under pressures of between 10 and 20 bar, preferably about 15 bar for the preferred temperatures. Butane boils lower than hexane, and therefore the regeneration of the butane can be accomplished under a pressure of about 11 bar, and at more importantly sump temperatures at which unsaturated hydrocarbons, e.g. diolefins, do not as yet polymerize. Thus it is possible to feed a portion of resultant concentrate to further separation while already under an initial superatmospheric pressure. The refrigeration can be made available at moderately low temperatures readily and inexpensively by the propylene cycle which is necessary in any case in the low-temperature separation stage.

When using butane and hexane as the scrubbing media, pressures of between about 10 and 20 bar are employed in the scrubbing columns. If the waste gas to be processed is supplied at a lower pressure, then it is merely necessary to replace the scrubbing media by higher homologs.

According to a further embodiment of the process of this invention, the loaded scrubbing medium of the first scrubbing stage is freed from the $C_3$-hydrocarbons by stripping, and the remaining scrubbing medium is withdrawn and, by heating, $C_4$- and higher hydrocarbons are vaporized therefrom. The resultant gas is used as the stripping gas for removing the $C_3$-hydrocarbons. For this purpose the separation of the $C_3$-hydrocarbons from the scrubbing medium is preferably conducted in a $C_3/C_4$-separating column mounted above a separating column for higher hydrocarbons, so that the vapors produced in the last-mentioned separating column rise through the liquid in the $C_3/C_4$-separating column.

In another embodiment of the process of this invention, the enrichment of the olefins in the first process stage is effected with the use of regenerators. In such a method, several cyclically operated regenerators are used. The regenerators are traversed by the gaseous stream during the first or loading phase, cooling said gaseous stream thereby. The components condensed therefrom during the cooling step settle on the surface of the regenerator packing while uncondensed components are withdrawn. In a subsequent purge phase, the condensed components are then revaporized by a stream of purge gas and driven out. Conventionally, a cooling phase follows such a purge phase, during which the regenerator is cooled down to such low temperatures that condensation of the components to be separated takes place in the subsequent, new loading phase. Such a regenerator process is preferably conducted with the use of at least three cyclically interchangeable regenerators.

In the recovery of low-molecular weight olefins according to this invention from a gaseous stream consisting essentially of components having a lower boiling point than the olefins, for example hydrogen, carbon monoxide, nitrogen, and methane, the olefins and higher-boiling components of the gaseous stream are condensed while flowing through regenerators and are thus retained. In such a mode of operation, it is advantageous to proceed with the cooling of the gaseous stream in the regenerators to such a point that the olefins are essentially completely condensed, so that in a subsequent purge phase the purge stream can remove the olefins at an enriched concentration. It proved to be advantageous to cool the gaseous stream to such a degree that $C_2$-hydrocarbons are condensed to an extent of at least 95%, preferably 99% or more. A substantial further cooling is not only economically unattractive owing to the increased demand for refrigeration resulting in an only minor rise in the olefin yield, but also leads in many cases to a reduction in the olefin concentration in the condensate, since the lower-boiling components, e.g., methane, are increasingly condensed.

To obtain the olefin-rich fraction during a purge phase, it is advantageous to employ as the purge gas a partial stream of the gaseous stream not condensed during a loading phase. Since the purge step takes place advantageously under a lower pressure than the loading procedure, only a small amount of scavenging (purge) gas is generally required, so as to mitigate dilution of the olefin-rich condensed fraction with lower-boiling components.

While the loading of the regenerators is conducted in a pressure range between about 5 and 15 bar, preferably between 8 and 10 bar, the pressure during a purge phase is suitably between 0.1 and 2.0 bar, for example approximately at atmospheric pressure. The purge operation conducted under such low pressures, preferably 0.2 to 1.3 bar, has the advantage that the amount of scavenging gas is reduced and thus the dilution of the components to be recovered is decreased; conversely, extremely low subatomspheric pressures entail high costs.

In an advantageous embodiment of the process of this invention, the refrigeration requirement for operating the regenerators is covered at least in part by engine expansion of the uncondensed, cold gaseous stream or of a partial stream thereof, In a preferred embodiment of the technique, the refrigeration demand is supplied by engine expansion of the purge gas stream, branched off from the uncondensed gaseous stream.

BRIEF DESCRIPTION OF THE DRAWINGS

Additional details of the invention will be described hereinbelow with reference to two preferred embodiments schematically illustrated in the figures. In both examples, the waste gas from a Fischer-Tropsch synthesis is employed as a source for the olefins to be obtained.

In the drawings.

DETAILED DESCRIPTION OF THE DRAWINGS

Figure 1:
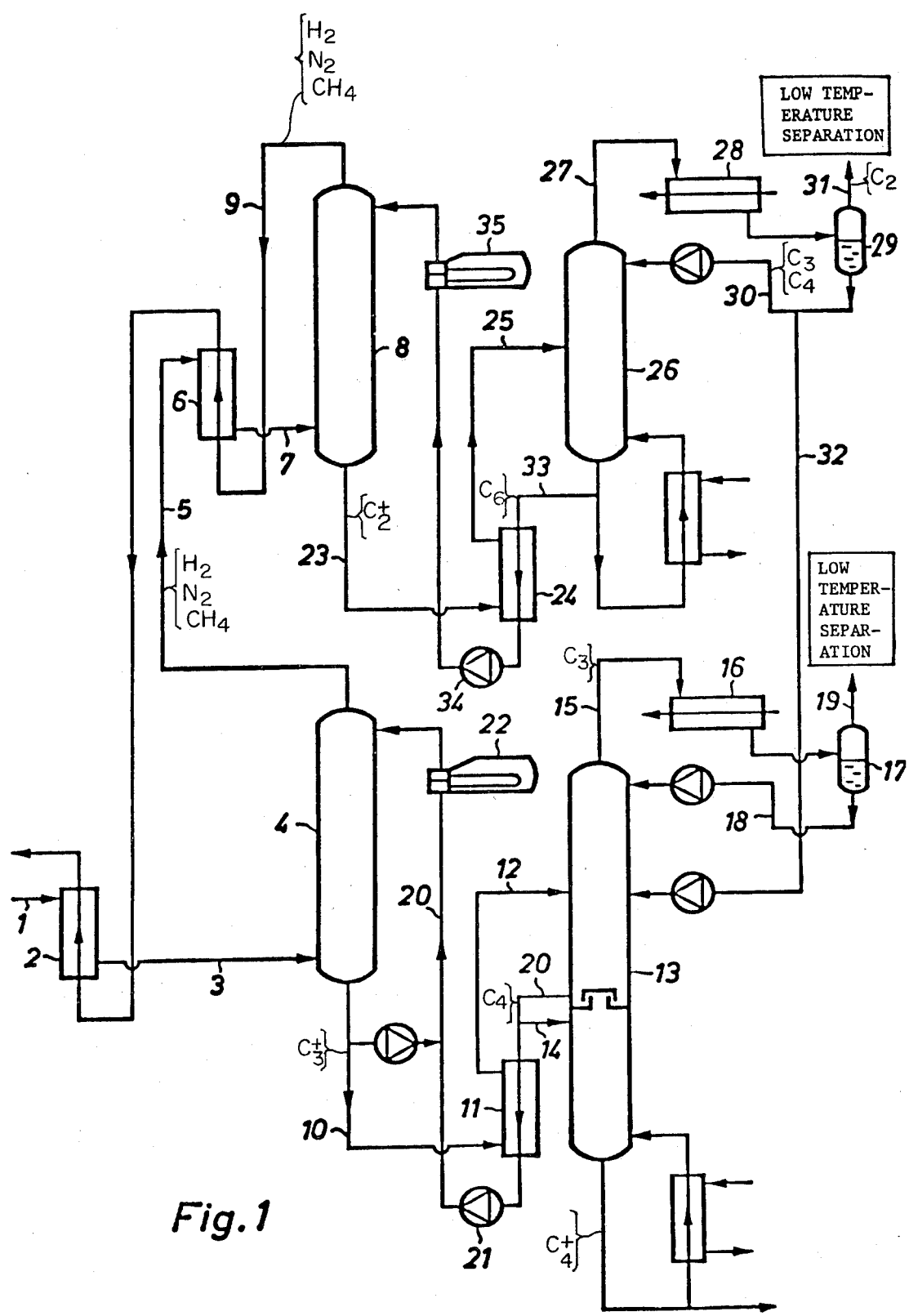
FIG. 1 is a schematic drawing of a first embodiment wherein the olefins are enriched in the first process stage by a scrubbing step.

Via conduit 1 of the embodiment shown in FIG. 1 4,461.5 kmol/h of waste gas from a Fischer-Tropsch synthesis, from which the carbon dioxide, initially present in an amount of 47 mol-% in the waste gas, had been conventionally removed in a scrubbing column, not shown, is introduced under a pressure of 15 bar and at a temperature of about 30° C. into a heat exchanger 2. The gas is not compressed before entering the scrubbing stage, since it already has the desired pressure of 15 bar from the Fischer-Tropsch synthesis. In heat exchanger 2, the gas is cooled to about 5° C. countercurrently to scrubbed gas and then passes via conduit 3 into the bottom of the first scrubbing stage 4. The waste gas has the composition set forth in Table 1.

In the scrubbing column 4, the gas is scrubbed countercurrently to downflowing liquid butane at 15 bar, said liquid having entered the column at −20° C. The major portion of the $C_{3+}$-hydrocarbons contained in the gas is thereby removed from the gaseous feedstream (F-T waste stream). The gas exiting from the head of the scrubbing column 4, the composition of this gas being derivable from Table 1, has a temperature of about −15° C. and is conducted via conduit 5 into a heat exchanger 6. In the latter heat exchanger, the gas is again cooled counter-currently to scrubbed gas and then passes via conduit 7 into the bottom of the second scrubbing column 8, this column operating at about 14 bar due to minor pressure drops between this column and the scrubbing column 4. In the scrubbing column 8, $C_2$-hydrocarbons and higher hydrocarbons still present in the gas are scrubbed out by means of entering hexane at −40° C. in a countercurrent operation. The scrubbed gas having the composition set forth in Table 1 exits from the scrubbing column 8 with a temperature of about −40° C. and is removed via conduit 9 and via the heat exchangers 6 and 2.

As can be seen from Table 1, all $C_2$- and higher hydrocarbons contained in the feedstream are completely scrubbed out except for minute amounts of $C_2$-hydrocarbons. The thus-scrubbed gas still contains small amounts of hexane due to saturation from the scrubbing medium.

From the $C_4$-scrubbing stage of the first scrubbing column 4, the scrubbing medium, loaded with $C_{3+}$-hydrocarbons, is withdrawn at the sump via conduit 10 and fed into a heat exchanger 11. In the latter, the loaded butane is warmed countercurrently to regenerated butane and conducted via conduit 12 into the upper part of a separating colum 13, said column having a bottom part and an upper part which are separated from each other with regard to the liquid flow. Both parts are supplied with bubble trays for intimately contacting the downflowing liquid with the raising vapours in the column.

In the upper part of column 13, $C_3$-hydrocarbons and all lower-boiling components are separated overhead. The scrubbing medium is discharged from the bottom zone of the upper part of the column via conduit 20. A portion of the scrubbing medium is fed into a heat exchanger 22 via pump 21 and conduit 20 and, after cooling to about −15° C., in heat exchanger 22, reintroduced into column 4 as the scrubbing medium. The other portion is introduced via conduit 14 into the lower portion of column 13; from the sump of this column, there are withdrawn $C_{4+}$-hydrocarbons. The overhead of the bottom part of this column comprising gaseous $C_4$-hydrocarbons is fed as heating vapor to the upper part of column 13.

The gas, enriched with $C_3$-hydrocarbons leaves the separating column 13 overhead at about 30° C. and is conducted via conduit 15 to a heat exchanger 16 wherein residues of higher-boiling hydrocarbons are condensed and separated in phase separator 17. The condensates pass via conduit 18 as reflux liquid back into the separating column 13 whereas the gas rich in $C_3$ is conducted at a pressure of about 12 bar via conduit 19 into a low-temperature separation system, not shown. The gas rich in $C_3$ has the composition inducated in Table 1.

The scrubbing medium of the second scrubbing stage, for exmple hexane, is regenerated in the same way. The loaded hexane at a temperature of about −30° C. leaves the sump of the scrubbing column 8 via conduit 23 and passes into a heat exchanger 24 wherein it is warmed countercurrently to regenerated hexane, whereupon it is conducted via conduit 25 after throttling in throttling means (not shown) to a pressure of about 5 bar into the middle of a separating column 26. In the latter, the $C_2$- and any remaining residues of higher hydrocarbons are heated in the reboiler to about 120° C., vaporized therein, and withdrawn as overhead at about 30° C. via conduit 27 and then conducted into a heat exchanger 28. In this latter heat exchanger, the $C_3$- and $C_4$-hydrocarbons are condensed. These condensates are separated in a separator 29 and recycled into the separating column 26 via conduit 30. The gas rich in $C_2$, the composition of which can be derived from Table 1, is conducted from separator 29 via conduit 31 into a low-temperature separation system, not illustrated.

Part of the condensate, especially the $C_4$-hydrocarbons, can be branched off from conduit 30 and passed to the same level as conduit 12 and fed via conduit 32 into the separating column 13.

Part of the thus-regenerated hexane is passed to the reboiler at the sump of the separating column 26, and the other part is withdrawn via conduit 33 and cooled in heat exchanger 24 countercurrently to loaded hexane. Via pump 34, the regenerated hexane is finally passed into another heat exchanger 35 wherein it is cooled to about $-40°$ C. and introduced at the head of the scrubbing column 8 into the scrubbing stage.

As can be seen from Table 1, a $C_2$-enriched gas is obtained by the use of the process of this invention, whith about 60% $C_2$-hydrocarbons, and a $C_3$-enriched gas is furthermore obtained with about 60% $C_3$-hydrocarbons. The high olefin proportion in these fractions can be separated in the usual way from the remaining components in low-temperature separation plants, and can be obtained as the desired product of the process.

Figure 2:
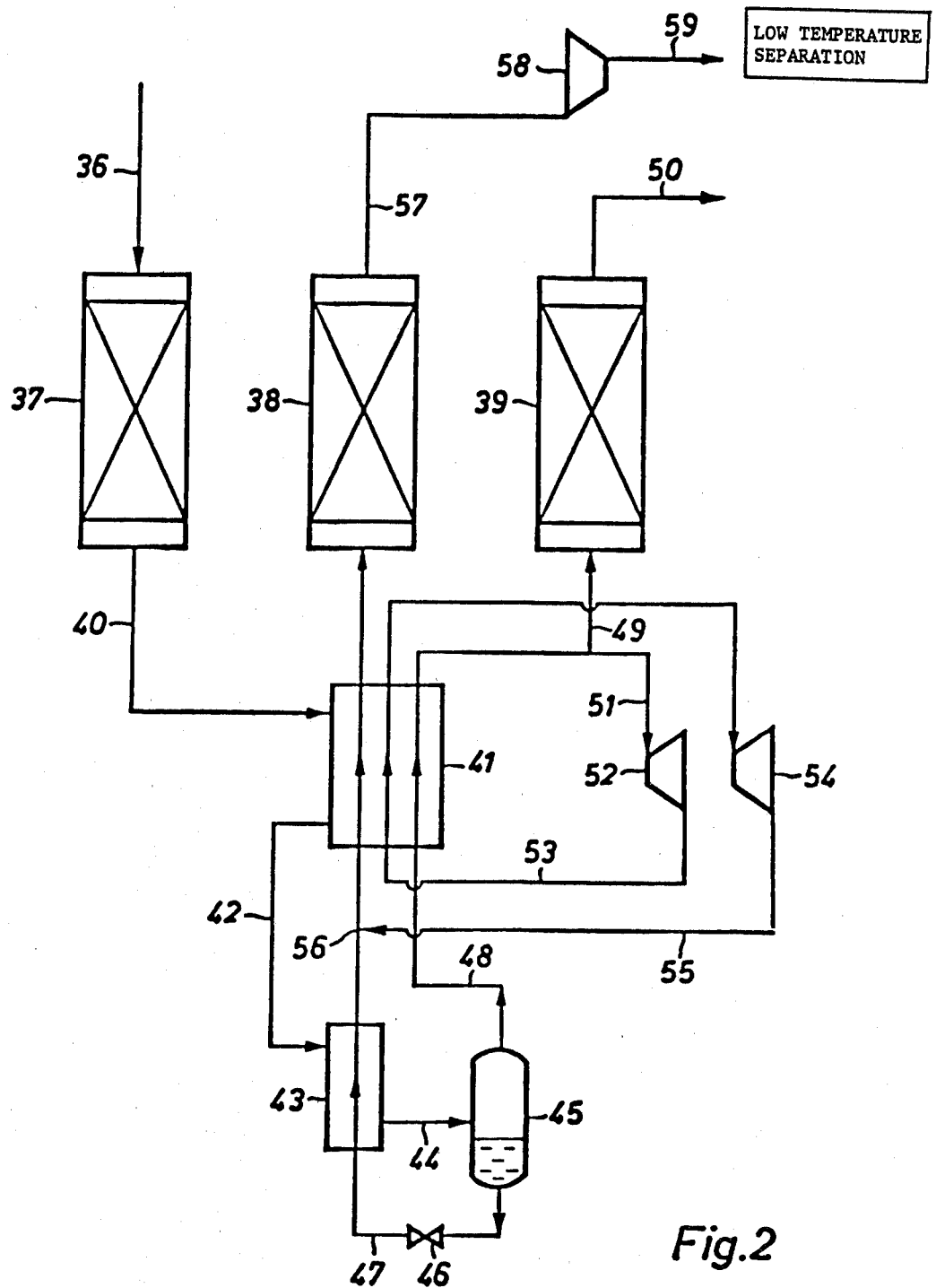
FIG. 2 is a schematic drawing of an embodiment wherein the olefins are enriched in the first process stage by the utilization of regenerator means.

In the embodiment illustrated in FIG. 2, the starting material is the same amount of a gaseous stream having the same composition as in the aforedescribed embodiment. The waste gas of the Fischer-Tropsch synthesis, from which carbon dioxide has again been removed in a preceding process stage, not illustrated, is conducted via conduit 36 into a first of three parallel-connected regnerators 37, 38 and 39. The regenerators are in communication with one another via a conduit system, not shown in the figure, in such a way that by operating various valves a cyclic interchangeability of the operating conditions of the individual regenerators is made possible.

The feedstream fed via conduit 36 is under a pressure of about 10 bar and is introduced into the regenerator 37, the packing of which had been cooled in a preceding process stage by a specific temperature difference. During cooling of the gas to about $-150°$ C., all $C_2$- and higher hydrocarbons are condensed and settle on the regenerator packing. The gas exiting from the cold regenerator end via conduit 40 and having the composition set forth in Table 2, is conducted through heat exchanger 41 through conduit 42, and through heat exchanger 43, the gas being cooled by about a further 3° C. during this procedure. The gas is then passed via conduit 44 into a phase separator 45 wherein additional condensate, formed during the cooling step, is separated. This condensate is withdrawn via the conduit 47, equipped with a valve 46, and after being warmed in heat exchangers 43 and 41, is fed into regenerator 38. The gaseous phase from separator 45 is introduced via conduit 48 to the heat exchanger 41 and thereafter subdivided into two partial streams. The largest part of this gaseous stream is introduced via conduit 49 into regenerator 39 wherein it is warmed and then leaves the system discussed herein via conduit 50 at a pressure of about 5 bar. A smaller portion of the gas warmed in heat exchanger 41 from conduit 48 is conducted via conduit 51 to an expansion turbine 52 and is work expanded therein with production of refrigeration. The thus-cooled, partially expanded gas passes via conduit 53 again into heat exchanger 41 and transfers its cold content to the gaseous stream in conduit 40. After reheating, further expansion is effected in expansion turbine 54 to obtain additional cold for covering the refrigeration demand of the process. The gas, expanded to about 1.1 bar, is conducted via conduit 55 to conduit 47 and is combined at 56 with the expanded condensate from separator 45. After being reheated in heat exchanger 41, this stream is conducted through regenerator 38 and serves to absorb the condensates precipitated in a preceding cycle. The gas withdrawn via conduit 57 during such a purge cycle is the fraction enriched with olefins which, after compression in a compressor 58, is conducted via conduit 59 to a low-temperature separation system. The composition of this fraction can be seen from Table 2.

The aforedescribed process with three regenerators is especially advantageous with an intake pressure of the compressor 58 of 1.1 bar, since the required amount of purge gas corresponds precisely to the quantity of gas which must be expanded in turbines 52, 54 for covering the refrigeration losses.

In a modification of the described regenerator process, the recovery of the olefin-enriched fraction condensed in a regenerator can be effected by purging at a lower pressure, for example at 0.1 bar. Such a modification has the advantage that the condensed hydrocarbons are driven out by a smaller quantity of scavenging gas and thus are obtained in a more concentrated form. Due to the lower requirement of purge gas, though, it is impossible to cover the refrigeration losses of such a method by expansion of the purge gas. It is therefore advantageous in such a case either to resort to external refrigeration or to select a process with four regenerators wherein the remainder of the waste gas stream expanded to cover the refrigeration requirement is introduced into the fourth regenerators.

The low-temperature separation system not illustrated in detail in the drawing is conventional and is described in the following references incorporated herein: Information Leaflets "$C_2H_4$-Plant for production of ethylene, propylene, acetylene, butadiene, gasoline and aromatics" and "$C_2H_4$, $C_3H_6$-Plant for the production of ethylene and propylene," published 1978 by Linde A. G. Further relevant references are German Pat. No. 2509689. U.S. Pat. No. 4,218,229 and copending U.S. patent application Ser. No. 082,452, filed Oct. 9, 1979.

TABLE 1

| | Gas After $CO_2$ Removal | Gas After $C_4$ Scrubbing Step | Gas After $C_6$ Scrubbing Step | $C_3$ Enriched Gas | $C_2$ Enriched Gas | $C_{4+}$ |
|---|---|---|---|---|---|---|
| $H_2$ | 56.24 | 65.31 | 72.49 | 2.45 | 6.75 | — |
| $N_2 + CO$ | 9.28 | 10.68 | 11.56 | 1.12 | 4.06 | — |

TABLE 1-continued

| | Gas After $CO_2$ Removal | Gas After $C_4$ Scrubbing Step | Gas After $C_6$ Scrubbing Step | $C_3$ Enriched Gas | $C_2$ Enriched Gas | $C_{4+}$ |
|---|---|---|---|---|---|---|
| $CH_4$ | 14.66 | 16.34 | 15.81 | 5.42 | 25.37 | — |
| $C_2H_4$ | 3.81 | 3.04 | 0.01 | 10.26 | 34.51 | — |
| $C_2H_6$ | 3.13 | 2.50 | 0.01 | 8.42 | 28.35 | — |
| $C_3$ | 7.14 | 0.08 | — | 59.94 | 0.96 | — |
| $C_4$ | 3.22 | 2.05 | — | 12.39 | — | 42.05 |
| $C_{5+}$ | 2.52 | — | 0.12 | — | — | 57.95 |

(Data in Mol-%)

TABLE 2

| | Gas After $CO_2$ Removal | Waste Gas From Enrichment (Conduit 50) | Concentrate From Enrichment (Conduit 57) |
|---|---|---|---|
| $H_2$ | 56.24 | 73.18 | 27.09 |
| $N_2 + CO$ | 9.28 | 11.72 | 5.09 |
| $CH_4$ | 14.66 | 15.04 | 14.02 |
| $C_2H_4$ | 3.81 | 0.06 | 10.27 |
| $C_2H_6$ | 3.13 | — | 8.48 |
| $C_3H_6$ | 5.83 | — | 15.88 |
| $C_3H_8$ | 1.31 | — | 3.56 |
| $C_4$ | 3.22 | — | 8.75 |
| $C_{5+}$ | 2.52 | — | 6.86 |

(Data in Mol-%)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for recovering $C_2$-$C_4$ olefins from a gaseous feedstream obtained from a Fischer-Tropsch waste gas containing about 2-3 mol % ethylene or propylene, said process comprising in a first process stage, scrubbing said gaseous feedstream with a $C_4$-$C_8$ liquid hydrocarbon, to absorb said olefin therein and recovering from said liquid hydrocarbon a gaseous stream, the weight percent concentration of said olefins in said gaseous stream being at least about 25%; and in a second process stage, recovering said olefins from said gaseous stream by a low-temperature separation, and wherein said Fischer-Tropsch waste gas is subjected to a carbon dioxide separating step before entering the first stage.

2. A process according to claim 1, wherein the olefins are enriched in the first process stage to more than 35 mol-%.

3. A process according to claim 1, said gas scrubbing stage being a two-stage scrubbing process conducted with a temperature which is lower in the second scrubbing stage than in the first scrubbing stage, differing scrubbing media being employed in the two scrubbing stages, which scrubbing media are regenerated separately from each other and are recycled into the respective scrubbing stages.

4. A process according to claim 3, wherein the scrubbing media employed are, in the first scrubbing stage, $C_4$- or higher hydrocarbons and, in the second scrubbing stage, $C_6$- or higher hydrocarbons, the second stage scrubbing media having a higher normal boiling point than said first stage.

5. A process according to claim 4, wherein the scrubbing medium in the first scrubbing stage is butane and the scrubbing medium in the second scrubbing stage is hexane.

6. A process according to claim 4, wherein in the first scrubbing stage, $C_3$- and higher hydrocarbons are substantially quantitatively scrubbed out and, in the second scrubbing stage, $C_2$-hydrocarbons are substantially quantitatively scrubbed out.

7. A process according to claim 4, wherein in the first scrubbing stage, $C_3$- and higher hydrocarbons are scrubbed out at $-20°$ C. and, in the second scrubbing stage, $C_2$-hydrocarbons are scrubbed out at $-40°$ C.

8. A process according to claim 4, the hydrocarbons in both scrubbing stages being scrubbed out at approximately the same pressures ranging between 10 and 20 bar.

9. A process according to claim 4, further comprising stripping $C_3$-hydrocarbons from loaded scrubbing medium of the first scrubbing stage, withdrawing remaining scrubbing medium, heating said remaining scrubbing medium to evolve $C_4$- or higher hydrocarbons out and utilizing resultant evolved gas for said stripping of the $C_3$-hydrocarbons.

10. A process according to claim 9, wherein said stripping of $C_3$-hydrocarbons from the scrubbing medium of the first scrubbing stage is conducted in a $C_3/C_4$-separating column, a second separating column for higher hydrocarbons being placed underneath said $C_3/C_4$ separating column, the vapors from this second separating column rising through the liquid in the $C_3/C_4$-separating column and functioning as reboiler vapor.

11. A process for recovering $C_2$-$C_4$ olefins from a gaseous feedstream obtained from a Fischer-Tropsch waste gas containing 2-3% ethylene or propylene, said process comprising in a first process stage partially condensing said feedstream in at least one of several cyclically operated and interconnected regenerators to condense out olefins in said regenerator and then removing said condensed out olefins therefrom as a gaseous stream having a weight percent concentration of said olefins of at least 25%; and in a second process stage recovering said olefins from said gaseous stream by a low temperature separation, and wherein said Fischer-Tropsch waste gas is subjected to a carbon dioxide separating step prior to entering the first stage.

12. A process according to claim 11, wherein at least three regenerators are employed.

13. A process according to claim 11, wherein the feedstream is a gaseous stream consisting essentially of components having a lower boiling point than the olefins, and comprising substantially entirely condensing the olefins and any corresponding paraffins during a loading phase of the regenerators while the gaseous feedstream flows therethrough, and revaporizing said olefins and any corresponding paraffins by passing a purge gas through said regenerator, and conducting resultant purge gas containing the olefins to the second process stage.

14. A process according to claim 13, wherein said gaseous feedstream is cooled during a loading phase to a temperature at which the $C_2$-hydrocarbons are condensed to an extent of at least 95%.

15. A process according to claim 13, wherein a partial stream of uncondensed feedstream withdrawn from the loading phase is utilized as the purge gas stream.

16. A process according to claim 15, further comprising engine expanding said purge gas stream to provide make-up refrigeration for the regenerators.

17. A process according to claim 13, further comprising engine expanding of at least one portion of the uncondensed gaseous feedstream withdrawn from the loading phase to provide make-up refrigeration for said regenerators.

18. A process according to claim 13, wherein purge gas pressure is 0.1–2.0 bar.

19. A process according to claim 13, wherein the gaseous feedstream in the first process stage is under a pressure of between 5 and 15 bar.

20. A process according to claim 11, wherein the olefins are enriched in the first process stage to more than 35 mol-%.

* * * * *